United States Patent [19]
Griffiths et al.

[11] Patent Number: 4,863,668
[45] Date of Patent: Sep. 5, 1989

[54] METHOD OF FORMING FIBRIN-COLLAGEN NERVE AND BODY TISSUE REPAIR MATERIAL

[75] Inventors: Russell H. Griffiths, St. Louis, Mo.; Kenneth W. Horch; Larry J. Stensaas, both of Salt Lake City, Utah

[73] Assignee: University of Utah, Salt Lake City, Utah

[21] Appl. No.: 247,728

[22] Filed: Sep. 22, 1988

[51] Int. Cl.⁴ .............................................. B29C 41/14
[52] U.S. Cl. .................................... 264/512; 264/233; 264/255; 264/307; 128/334 R
[58] Field of Search ......... 128/DIG. 8, 334 C, 334 R; 264/302, 255, 307, 233, 512

[56] References Cited

U.S. PATENT DOCUMENTS

| | | | |
|---|---|---|---|
| 2,173,939 | 9/1939 | Sidnell | 264/255 |
| 2,525,272 | 10/1950 | Rhoton | 264/255 |
| 3,036,341 | 5/1962 | Taylor | 128/334 R |
| 3,526,228 | 9/1970 | Lyng | 128/334 R |
| 3,906,071 | 9/1975 | Cook et al. | 264/255 |
| 4,215,200 | 7/1980 | Miyata et al. | 128/334 R |
| 4,406,853 | 9/1983 | Miyata | 264/307 |
| 4,453,939 | 6/1984 | Zimmerman et al. | 604/304 |
| 4,565,663 | 1/1986 | Errede et al. | 264/122 |
| 4,759,764 | 7/1988 | Fawcett et al. | 128/334 R |
| 4,770,176 | 9/1988 | McGreevy et al. | 128/334 R |

Primary Examiner—Jan H. Silbaugh
Assistant Examiner—Allan R. Kuhns
Attorney, Agent, or Firm—K. S. Cornaby

[57] ABSTRACT

A method of forming material including alternating layers of fibrin and collagen, formed into tubes, is disclosed for use in repairing transected nerve fibers either by tubulization of the approximated nerve ends, or as an artificial graft which are placed in the severed ends of the nerve, for promotion of nerve growth and regeneration. The new material is treated to reduce antigenicity and is resorbed into the body following regeneration of the nerve fibers.

9 Claims, 1 Drawing Sheet

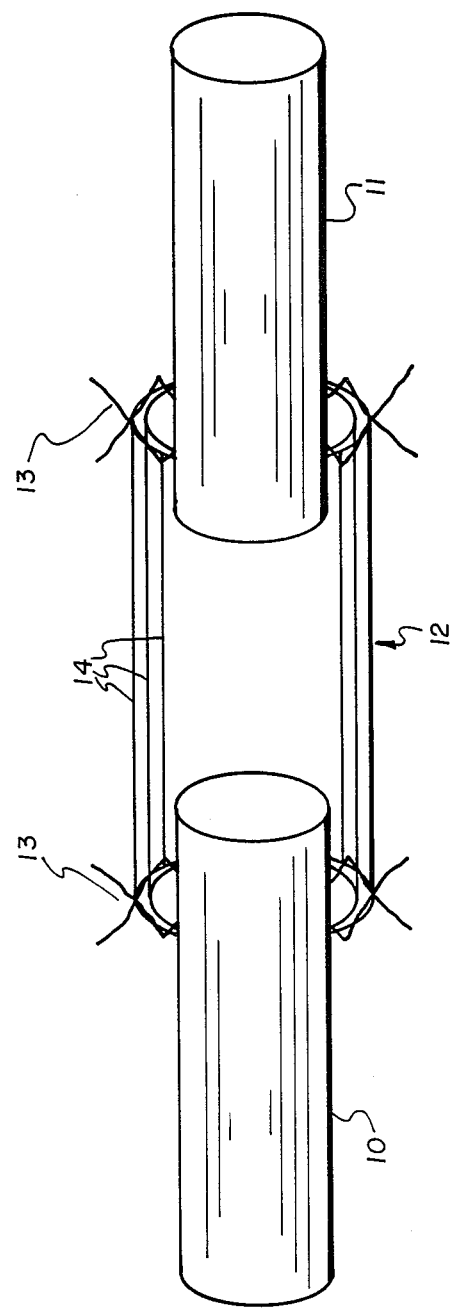

METHOD OF FORMING FIBRIN-COLLAGEN NERVE AND BODY TISSUE REPAIR MATERIAL

BACKGROUND OF THE INVENTION

The invention relates, primarily, to the repair of peripheral nerves which have been severed through accident or, perhaps, required medical procedure. Peripheral nerve fibers which have been severed may, under some circumstances, regenerate if proper steps are taken to promote such regeneration. In the past, several techniques have been utilized to attach and promote nerve regeneration.

In cases where the gap between proximal and distal ends of the severed nerve has been small enough, a technique of suturing the two ends together has been used in order to promote regeneration of nerve fibers across the gap. Notably, this technique cannot be used in applications where the gap is greater than one centimeter. This method of bridging often proves unsatisfactory because the suturing process can damage both the nerve fibers and the epineurium, and the sutures may produce excessive foreign body reactions. Additionally, the surgical manipulations required to effectuate the repair may induce the formation of excessive scar tissue which frequently interferes with growth of the proximal stump axons into the distal nerve stump.

In cases where the gap between the proximal and distal ends of the severed nerve cell has been too great to suture the two ends together, a method of spanning the gap has been used. In one application, a graft of autologous sural or other nerve tissue has been taken from elsewhere in the body to serve as the bridge between the severed ends. This method has the unfortunate effect of sacrificing normal nerve tissue from the donor area. Many procedures of bridging the gap have been tried in the past making use of synthetic materials such as tantalum, cellulose polymer, and silicone, but these materials have caused a capsule to form and, in some cases, fibrosis or calcification. Additionally, silicone nerve repair devices have been shown to require careful matching of the tube size to the size of the nerve being repaired. Silastic ® tubes are also reported to result in nerve fiber damage which has resulted over time because of the non-bioresorbable nature of the material.

Antigenic and other reactions which are experienced with use of synthetic materials have been avoided through use of biopolymers which are biodegradable within the body. Many biopolymers have been tested including a fibrinogen and fibrin mixture, and collagen. However, these materials have also proven unsatisfactory because of inadequate vascularazation, adverse tissue reactions, fragmentation of the material, or excessive persistence in the body.

The invention disclosed herein is a biodegradable tubulization material comprised of fibrin and collagen layers which effectively overcomes the problems experienced with other techniques and materials used for repairing nerves.

SUMMARY OF THE INVENTION

The present invention is made of layers of collagen and fibrin polymers, treated to reduce antigenicity and to control the rate of biodegradation following implantation. The material, in the preferred embodiment, is made into tubes by coating a mandrel with alternating layers of fibrin and collagen. Any number of layers may be produced depending upon the proposed application, and the tubes produced by the process are cut to the length dictated by the gap to be spanned. The diameter of the tube may be selected by varying the size of mandrel used for production of the tube.

The tubes produced by this method can be used either for tubulization of an end-to-end anastamosis of transected nerve, in other words, a cuff encircling the union of severed nerve cell ends, or it may be used for bridging gaps where end-to-end union cannot be achieved. In the former application, a cuff encircling the juncture of nerve ends protects the union and enhances healing. In the latter application, the proximal and distal ends of the transected nerve are inserted into the ends of the fibrin-collagen tube and sutured to the epineurium of the proximal and distal stumps. The tube provides a directed pathway for the proximal nerve fibers to follow in regenerating to the distal stump. In addition to providing a pathway for growth, the fibrin-collagen tube enhances the growth process. Under either application, the cuff or tube is resorbed into the body after the nerve has regenerated.

In the tube form as described, the fibrin-collagen may also be used in similar repair procedures involving vascular tissues. In other medical applications, the fibrin-collagen material may be made by layering the polymers in a flat sheet. In this form, the material may be used as a covering for skin grafts to cover burns or other areas which have been excoriated.

It is an objective of this invention to provide a highly biocompatible material suitable for enhancing nerve regeneration which is resorbed into the body after regeneration is complete.

It is further an objective of this invention to provide a material for nerve regeneration which has reduced or absent antigenicity.

Another objective of this invention is to provide a biodegradable scaffold for new collagen to be formed in continuity with the epincurial sheath as a source of structural reinforcement for the regenerating nerve.

Another objective of this invention is to provide a material for nerve regeneration which is preformed into varying diameters, lengths, and thicknesses to facilitate the ease of surgical use.

It is also an objective of this invention to provide a material for nerve regeneration which promotes proper nerve fiber regeneration and allows proper revascularization of the area.

These and other objectives and uses of the invention will become more clear in the following discussion.

BRIEF DESCRIPTION OF THE DRAWING

The preferred application of the invention is illustrated by the following drawing:

FIG. 1 is a perspective view of the fibrin-collagen tube with the proximal and distal ends of a severed nerve inserted in either end thereof.

DETAILED DESCRIPTION OF THE PREFERRED EMBODIMENT

The materials used for production of the fibrin-collagen tube are fibrinogen isolated from Cohn fraction 1, thrombin comprising 25% protein and 75% buffer salts with a pH of 5.8, Collagen of Type I or Type III (pepsinized), NaCl, a solution of $CaCl_2$ in Tris buffer of pH 7.2, and a solution made of 25% glutaraldehyde and 37.5% formaldehyde stock solutions.

The thrombin should first be dissolved in normal saline and then added to the CaCl₂ solution. The fibrinogen is dissolved in distilled water, as is the pepsinized collagen. Lastly, a solution of NaCl is prepared.

The production of the tube begins by polymerizing the fibrin by slowly adding the dissolved fibrinogen solution dropwise to the thrombin/CaCl₂ solution until cotton-like fibers form. A Teflon ® coated cylindrical mandrel, the diameter of which is approximately 30% larger than the diameter of the nerve to be repaired, is dipped in the solution so that the fibers adhere to it. The mandrel is spun and pressed against the wall of the container to provide a uniform coating until the solution clears.

Polymerization of collagen over the fibrin layer is achieved by dipping the coated mandrel in the collagen solution, followed by dipping the mandrel into the NaCl solution to precipitate the collagen.

The process of dipping the mandrel in the fibrinogen solution followed by dipping it in the collagen solution is repeated until the desired numbers of layers are achieved. When the desired number of layers is reached, the coated mandrel is placed in the solution of glutaraldehyde/formaldehyde at room temperature for 30 minutes. The coated mandrel is then washed in a large volume of distilled or deionized water. The tubes are then autoclaved in a large volume of normal saline for 30 minutes at 120° C. Thereafter, the tube is removed from the mandrel and is washed in agitated double distilled or deionized water until the residual aldehyde is removed. The tubes are then placed in vials containing normal saline, are sealed, and are autoclaved for 30 minutes at 120° C.

The tubes may be made by beginning with the collagen layer first, coated on a mandrel, followed by the fibrin layer, rather than the fibrin layer first as described above. The fibrin-collagen material may be made in flat sheets for use in other applications by coating each layer, as described above, on a flat nonadherent surface. Once made, the tubes or sheets may be stored at room temperature in sealed vials containing normal saline.

In application, the tubes made by this process are used to bridge the gap across severed peripheral nerves. As illustrated in FIG. 1, the proximal end 10 and distal end 11 of a severed peripheral nerve fiber are inserted into either end of the fibrin-collagen tube, generally at 12, and sutures 13 are taken to anchor the nerve in place while regeneration takes place. The multiple layers 14 of fibrin and collagen are illustrated.

We claim:

1. A method for production of material used in regeneration of nerve cells, comprising the steps of:
   preparation of a solution of thrombin,
   dissolution of fibrinogen in water;
   dissolution of pepsinized collagen in water;
   polymerization of fibrin by slowly adding said dissolved fibrinogen solution to said thrombin solution until cotton-like fibers form;
   dipping a smooth, nonadherent mandrel into said polymerized fibrin solution to coat a fibrin layer on said mandrel, and spinning said mandrel to promote uniform coating;
   polymerization of collagen over said fibrin layer on said mandrel by dipping said coated mandrel in said collagen solution, followed by dipping said mandrel in a NaCl solution;
   then placement of said coated mandrel in a solution of glutaraldehyde and formaldehyde at room temperature;
   then washing of said coating on said mandrel in water;
   then autoclaving of said coated mandrel in normal saline at 120° C.;
   then removal of a tube formed by said coating from said mandrel and washing of said tube to remove residual aldehydes; and
   placement of said tube in a vial containing a liquid medium, and autoclaving to form said material.

2. A method of producing material as set forth in claim 1 in which multiple alternating layers of fibrin and collagen are coated on said mandrel by repeating, alternatingly, the step of dipping of a teflon-coated mandrel into said polymerized fibrin solution and spinning said mandrel to promote uniform coating, and the step of polymerization of collagen over said fibrin layer by dipping said coated mandrel in said collagen solution followed by dipping said mandrel in a NaCl solution.

3. A method of producing material as set forth in claim 1, in which the preparation of said solution of thrombin comprises the steps of:
   solubilization of thrombin by dissolution in normal saline; and
   addition of said solubilized thrombin to a solution of CaCl₂ in Tris buffer.

4. A method of producing material as set forth in claim 1, in which the washing of said tube of material is accomplished by use of agitated double distilled water.

5. A method of producing material as set forth in claim 1, in which said liquid medium in which said tube is placed for final autoclaving is distilled water.

6. A method of producing material as set forth in claim 1, in which said liquid medium in which said tube is placed for final autoclaving is deionized water.

7. A method of producing material as set forth in claim 1, in which said liquid medium in which said tube is placed for final autoclaving is normal saline.

8. A method of producing material as set forth in claim 1, in which the water used in any step of the process is distilled water.

9. A method of producing material is set forth in claim 1, in which the water used in any step of the process is deionized water.

* * * * *